United States Patent [19]

Wacker

[11] 4,195,125

[45] Mar. 25, 1980

[54] PROCESS FOR OBTAINING INSULIN-PRODUCING ANIMAL CELLS

[75] Inventor: Adolf Wacker, Neu-Isenburg, Fed. Rep. of Germany

[73] Assignee: Hoechst Aktiengesellschaft, Frankfurt, Fed. Rep. of Germany

[21] Appl. No.: 971,526

[22] Filed: Dec. 20, 1978

[30] Foreign Application Priority Data

Dec. 22, 1977 [DE] Fed. Rep. of Germany ....... 2757169

[51] Int. Cl.$^2$ .............................................. A01N 1/02
[52] U.S. Cl. ...................................................... 435/2
[58] Field of Search ......................................... 195/1.8

[56] References Cited

PUBLICATIONS

Hollande — Chem. Abst. vol. 86 (1977) p. 40991f.
Ziegler et al — Chem. Abst. vol. 86 (1977) p. 168,788n.

*Primary Examiner*—Sam Rosen
*Attorney, Agent, or Firm*—Curtis, Morris & Safford

[57] ABSTRACT

A process for obtaining insulin-producing cells by fusing islet cells derived from an animal or human pancreas with cells growing in suspension.

3 Claims, No Drawings

PROCESS FOR OBTAINING INSULIN-PRODUCING ANIMAL CELLS

The present invention relates to a process for obtaining insulin-producing animal cells.

The cultivation of insulin-producing betacells derived from an animal or human pancreas in tissue cultures has been successful for a prolonged period of time. Therefore, attempts have been made to obtain novel permanent cells which are capable of producing insulin and which can be cultivated in suspension by fusion of the betacells with cells which can be kept and successfully propagated in tissue cultures. All these prior attempts have failed. For example, attempts to fuse betacells of rat origin with A9 cells using Sendai virus met with limited success (Jacob, M.: Diplomarbeit, Fachbereich Biologie, University of Frankfurt/Main (1973)).

It has now been found that an islet cell derived from an animal or human pancreas which cannot be cultivated can be fused with a cell growing permanently in suspension to form a new cell which can grow permanently in suspension and is capable of producing insulin. This fusion process can be carried out in the presence of a fusion-inducing agent, for example polyethylene glycol, and by using as a permanently growing cell a mutant that is hindered from further growth by a selective medium and can thus be removed from the cell culture after the fusion.

As insulin-producing cells there are used, for example, betacells derived from the pancreas of homothermals of rat, pig or human origin. As permanently growing cells there are used cells that divide in quick succession, for example the A9 cells (a clonal derivative of the L-cell of the mouse) or human HeLa-cells, clone S3AG1.

The insulin-producing cells and the permanently growing cells are fused by using a suitable agent such as polyethylene glycol, PEG.

However, the separation of the fused insulin-producing and permanently growing cells from the initially used cells has not been previously successful and as a consequence the novel cells obtained were overgrown by the permanently growing cells so that a further cultivation was no longer possible.

In the process of the invention those cells that do not produce insulin are hindered from growing by a suitable medium after the fusion and can then be removed from the culture. For this purpose HAT-medium may be used. Only the fused cells and the initially used insulin-producing cells remain in the tissue culture. However, the latter stop growing after several passes so that in the end only the fused cells remain. They continue to grow and to produce insulin.

The cells thus obtained can be used for the production of insulin.

The invention will be illustrated in the following Example:

EXAMPLE

Pancreas tissue was removed from 6-month-old pigs and was kept for 20 to 40 minutes in Earle's salt solution (ESL) supplement with 200 $\mu g$ penicillin and 200 $\mu g$ streptomycin/ml, at 4° C. The pancreas tissue was freed from connective tissue and fat, cut into pieces $1 \times 1$ mm in size with scissors and washed repeatedly prior to being digested with Collagenase. For the digestion, a 1 g portion of the tissue was incubated for 8 to 10 minutes at 30° to 37° C. with 1 ml Collagenase (17449 SERVA, Heidelberg, 0.6–0.8 U/mg) per ml ESL with shaking. To the resultant tissue suspension was added the double quantity of Dulbecco's MEM-modification (DMEM) supplemented with 10% calf serum and the supernatant was decanted after sedimentation of the tissue portions. This procedure was repeated using 4 to 6 portions of fresh Collagenase solution. The supernatants of the first and second enzyme treatments were discarded. The following Collagenase fractions contained islets, endocrine cell groups and single cells. These supernatants kept at room temperature were centrifuged after the last treatment, absorbed in a little DMEM and drawn up and syringed through a 20 G $1\frac{1}{2}$ cannule until all islets and endocrine cell groups had disintegrated into single cells (about 5 to 10 ml). Then the cell suspension was centrifuged and washed 3 to 4 times with DMEM supplemented with 10% calf serum and antibiotics. The cell suspension consisting of about 80% of B-cells, the remainder being A-, C- and D-cells, was taken up in 10 ml DMEM supplemented with 10% fetal calf serum and antibiotics at a concentration of about $5 \times 10^5$ cells/ml, seeded out in 10 cm Petri dishes (CORNING, Wiesbaden) and incubated for 24 hours at 37° C. in a 5% $CO_2$ atmosphere.

Fusion $5 \times 10^6$ pig cells and $1 \times 10^7$ A9 cells (a clonal derivative of the L-cell of the mouse) were detached from the Petri dishes by a trypsin treatment using 0.05% trypsin (LS-Labor Service, Munich) and 0.02% EDTA in a salt solution free of $Ca^{2+}$ and $Mg^{2+}$, mixed together and separated by centrifugation. The cell pellet was suspended by pipetting it 2 to 3 times using 0.5 ml PEG 6000 (SERVA, Heidelberg) as 50% solution in DMEM and was then incubated for 2 minutes at 37° C. The agglutinated cell mixture was dispensed in 100 ml DMEM supplemented with 10% calf serum and 6% Ficoll placed in a cylinder of 2 cm diameter. The contents of the cylinder were allowed to stand for 3 hours at 37° C. under sterile conditions, whereby the cells sedimented. The 10 ml bottom layer was taken up with a pipette, seeded out in DMEM in Petri dishes and incubated at 37° C. in a 5% $CO_2$ atmosphere. The fusion yield was about 5%. The A9 cells, the pig cells, the heterocaryotic cells and the hybrid cells were left for growth for 3 days, then the used medium was withdrawn with a pipette. The cultures were overlaid with HAT-medium (Exptl. Cell Res. (1966) 41, 190) in which A9 cells that had not fused stopped growing. After about 8 days the cultures were harvested by trypsinization and a small number of cells was again transferred to HAT-medium. In this process those cells that had not fused died as well. The hybrid clones had grown to full size in 3 to 4 weeks. Varying quantities of grown up hybrid cells were observed under the inverted phase contrast microscope. These clones comprising about 200 to 500 cells were placed in small steel cylinders 1.8 mm in diameter and were subjected to a trypsin treatment. The cell suspension was further cultivated in 6 cm Petri dishes.

The hybrid cells were propagated in culture flasks according to Roux (1200 ml) until the 35th passage was reached. After a trypsin treatment using a trypsin-EDTA solution (EDTA=ethylene diaminotetraacetic acid) a 150 ml portion of the cell suspension having a cell density of $1 \times 10^6$ per ml of medium was seeded out in a 250 ml culture flask according to MAY (Zentralbl.

Bakteriol. Abt. 1 Orig. (1964) 193, 306). The medium used was DMEM supplemented with 10% calf serum and 0.1 mg $ZnSO_4$/l. The stirring velocity was one rotation per second. The culture flask was placed in a water bath of 36° C. A 5% $CO_2$-air mixture was introduced into the culture by means of an aquarium pump by passing over a Millipore gas filter. A flow rate of 13 l/h was necessary in order to maintain a constant pH of 7.2. The number of cells had doubled every 2 to 3 days. Then approximately ⅓ of the cell suspension was withdrawn under sterile conditions and an identical quantity of medium was added. The cells that had been collected by centrifugation could be seeded out and continued to grow without difficulty. The insulin activity expressed in terms of immunologically measurable insulin in the supernatants of the collected cell suspensions (150 ml) depended on the quantity of glycose in the medium (300 mg %) and was found to be about 15 $\mu$u U IMI after 6 hours of cultivation.

What is claimed is:

1. A process for obtaining insulin-producing cells which comprises fusing islet cells derived from pancreas with A9 cells or human He-La-cells growing in suspension.

2. The process as claimed in claim 1, which comprises performing fusion in the presence of polyethylene glycol.

3. The process as claimed in claims 1 or 2, which comprises hindering those cells that do not produce insulin from further growing after the fusion by the addition of HAT-medium and removing them from the culture.

* * * * *